United States Patent [19]

Theodoropulos

[11] Patent Number: 4,873,318

[45] Date of Patent: Oct. 10, 1989

[54] OXAZINE-UREAS AND THIAZINE UREA CHROMOPHORS

[76] Inventor: Spyros Theodoropulos, 2964 Hickory St., Yorktown Heights, N.Y. 10598

[21] Appl. No.: 110,415

[22] Filed: Oct. 20, 1987

Related U.S. Application Data

[63] Continuation-in-part of Ser. No. 69,860, Jul. 6, 1987, abandoned, which is a continuation-in-part of Ser. No. 753,937, Jul. 11, 1985, Pat. No. 4,714,763.

[51] Int. Cl.$^4$ ............... C07D 265/38; C07D 279/36
[52] U.S. Cl. ................................ 530/387; 436/136; 530/389; 530/802; 530/391; 544/31; 544/37; 544/99; 544/103
[58] Field of Search ............... 530/487; 544/31, 37, 544/99, 103

[56] References Cited

U.S. PATENT DOCUMENTS

| | | | |
|---|---|---|---|
| 4,600,775 | 7/1986 | Theodoropulos | 544/99 |
| 4,714,763 | 12/1987 | Theodoropulos | 544/31 |
| 4,780,535 | 10/1988 | Theodoropulos | 544/99 |
| 4,789,742 | 12/1988 | Theodoropulos | 544/99 X |

*Primary Examiner*—Richard L. Raymond
*Attorney, Agent, or Firm*—Burgess, Ryan & Wayne

[57] ABSTRACT

Novel adducts of oxazine urea chromophors or thiazine urea chromophors with organic substrates are provided which are useful in analytical techniques for the detection and measurement of biological and clinical compounds of interest.

8 Claims, No Drawings

OXAZINE-UREAS AND THIAZINE UREA CHROMOPHORS

This application is a continuation-in-part of U.S. patent applicaton Ser. No. 753,937, filed July 11, 1985 now U.S.Pat. No. 4,714,703, a continuation in part Ser. No. 069,860 was filed July 6, 1987, now abandoned, both of which are incorporated herein by reference.

FIELD OF THE INVENTION

This invention relates to novel urea derivatives of oxazine type chromophors, such as, for example, Nile blue A and to thiazine type chromophors such as, toluidine blue O useful in the fluorescent labeling of organic substrates. The urea derivatives of the invention have the ability to react with compounds of biological or clinical interest to form adducts resulting in the fluorescent labeling of the compounds. The novel compounds are intended for use in analytical techniques for the detection and measurement of biological and clinical compounds of interest. Typical examples of such compounds are bacteria, viruses, enzymes blood groups, hormones and drugs.

DESCRIPTION OF THE PRIOR ART

It is known that fluorescent groups such as fluorescein isothocyanate can be introduced into biological compounds of intereset. Analytical techniques employing fluorescein frequently lack the requisite sensitivity for the detection and measurement of nanomolar or picomolar levels of organic substrates. The lack of sensitivity of techniques which employ fluorescein is believed to be due to a high degree of overlap in fluorescent excitation and emission spectra and to high background fluorescence exhibited by biological fluids. Furthermore, the applicability of fluorescein is limited since it only attaches to compounds having displacable amine moieties such as proteins, peptides or amino acids.

Accordingly, it is an object of the present invention to provide novel urea derivatives of oxazine type chromophors which may be readily coupled to compounds of clinical or biological interest to provide derivatives which exhibit intense fluorescence. A further object of the invention provides for fluorescent labeling of biological molecules which circumvent the limitations of background fluorescence implicated in immunological assays. Yet another object of this invention lies in the coupling of the novel moieties to form adducts with a broad spectra of biological and clinical compounds by facile and gentle chemical reactions.

Other objects and advantages of the present invention will become apparent from the following detailed description of the present invention.

While the invention is susceptible to various modifications and alternative forms, there will herein be described in detail the preferred embodiments. It is not intended to limit the invention to the specific forms disclosed. On the contrary, it is intended to cover all modifications and alternative forms falling within the spirit and scope of the invention as expressed in the appended claims.

SUMMARY OF THE INVENTION

The present invention is directed to novel urea derivatives of oxazine type chromophors which contain moieties which allow the coupling of these chromophors to a variety of biological molecules of clinical interest. The resulting derivatives provide intense fluorescent haptens, antigens, drugs and antibodies which can be used in the development of fluorescent analytical techniques. A number of oxazine type chromophors such as Cresyl violet, Brillinat cresyl blue, Nile blue A, oxazine, etc., have been derivatized through a urea linkage to functional derivatives without effectively changing the fluorescent characteristics (e.g. excitation, emission) of the subject chromophors. The basic structures of the urea-oxazines are structurally represented by the structural formulas I and II.

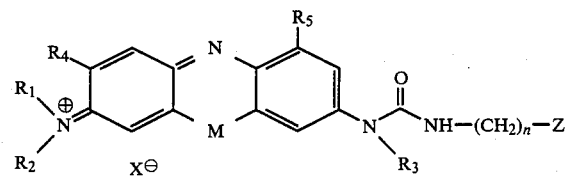

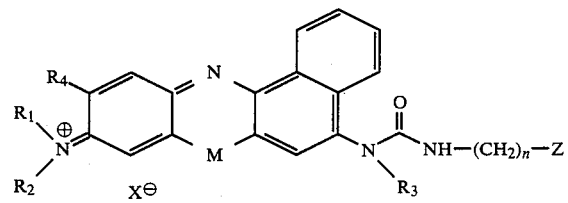

wherein M is O or S; $R_1$ and $R_2$ are aliphatic alkyl groups or hydrogen; $R_3$ is hydrogen or aliphatic alkyl group; $R_4$ is hydrogen, alkyl or amino; $R_5$ is hydrogen, amino or alkyl group; $X^-$ is an anion consisting of an organic or inorganic specie such as, for example, $Cl^-$, $Br^-$, $I^-$, $ClO_4^-$, $SO_4''$, $CH_3CO\ O^-$, $CH_3CH_2CO\ O^-$; n is 0–20; Z is $N=C=O$, $N=C=S$, carboxylic, primary or secondary amine, and when n=0, Z may be

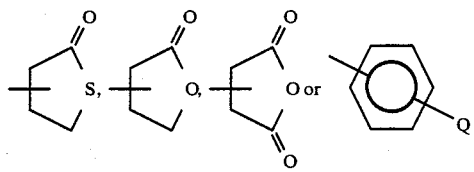

where Q is hydroxyl, amino, carboxylic, sulfhydryl, isocyanato, azido ($-N_3$), or the structural formula II.

Typical examples of oxazine and thiazine chromophors are shown below, both by structural formula and name.

Nile blue A
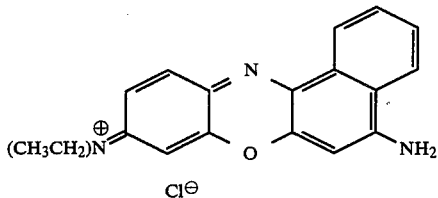

Toluidine blue O
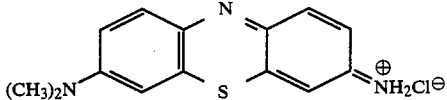

Brilliant cresyl blue
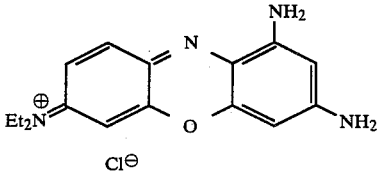

Cresyl Violet Acetate
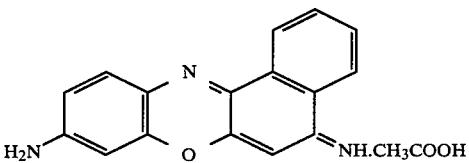

Azure A
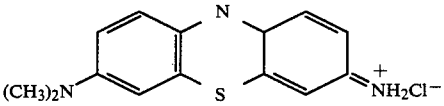

Azure C
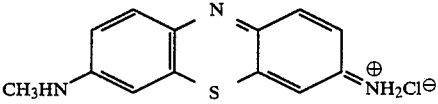

Thionin
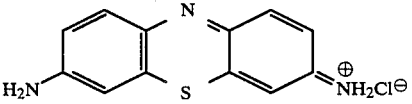

DETAILED DESCRIPTION OF THE INVENTION

The oxazinyl urea compounds of the invention are bi-functional. The oxazinyl urea moiety represented structurally as I and II

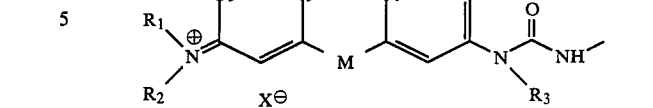

or

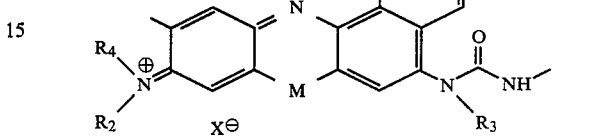

act as an ideal fluorescent agent due to its attractive fluorescence emission exhibited at wavelengths above 580 nanmoeters. The remaining moiety of the invention compounds, represented by the radical $-(CH_2)_n-Z$, where Z is an isocyanate, isothiocyante, lactone or thiolactone moiety, provides an active hydrogen bonding site and functions most suitably to promote coupling of the oxazinly urea with organic substrates of interest.

The oxazinyl and thiazinyl ureas of the invention were synthesized using known techniques. For example, the reaction of the oxazine and thiazine chromophors of the general formulas Ic or Id

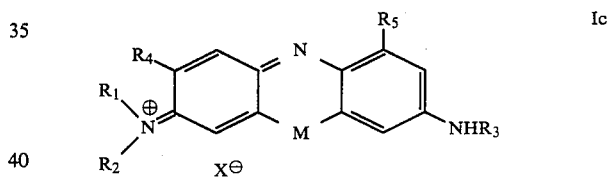

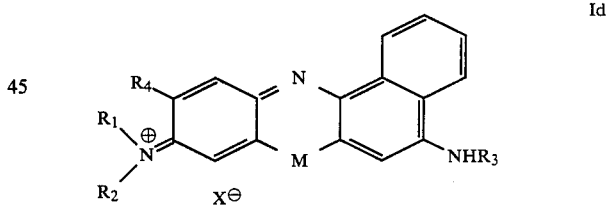

with a bi-functional isocyanate of the general formula:

$$O=C=N-(CH_2)_n-Z$$

wherein when n is 0, Z is lactone, thiolactone or succinic anhydride, and when n is 1 to 20, Z is isothiocyanate, isocyanate, blocked carboxylic or benzene derivatives such as

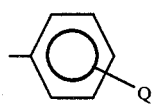

where Q is blocked primary or secondary amine, blocked carboxylic, isocyanate or isothiocyanate was preferred.

An example demonstrating the derivatization of Nile blue A is illustrated in the following equation:

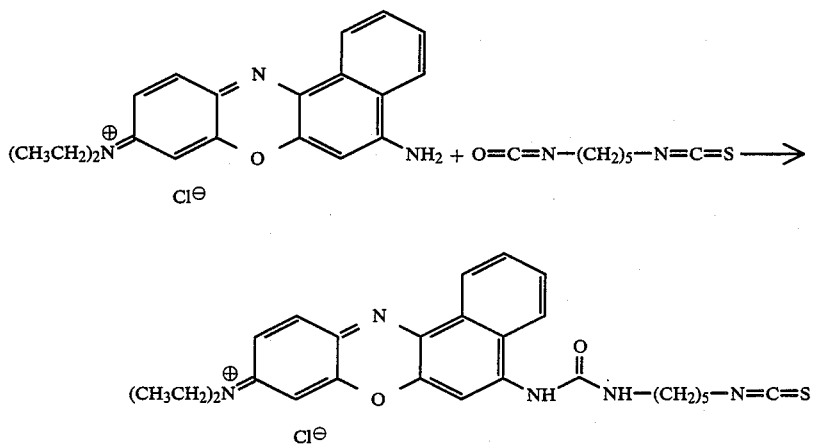

The synthesis was optionally performed in the presence of a solvent which was inert to the reaction partners such as aromatic hydrocarbons, e.g. benzene, toluene, xylene or aliphatic or aromatic chlorinated hydrocarbons, such as, esters, ketones or amides with pyridine being the preferred solvent. The temperature employed in the synthesis may range from 5° to 150° C. with ambient temperature being preferable.

The oxazinyl ureas of the invention may be reacted with any compound of interest capable, of course, of reacting with the Z radical. For example, any compound containing (in the classical sense) an active hydrogen group may be coupled to the oxazinyl ureas, e.g. any compound containing a hydroxyl, amino, sulfhydryl or carboxylic group can be utilized. Accordingly, a wide number of amino acids, peptides, proteins, enzymes, steroids, drugs, pesticides, various natural products, plant and animal hormones, polyamines, viruses, bacterial cells and other metabolites contain groups reactive with the Z radicals.

The oxazinal urea chromophors can be bound to organic substrates through the Z moiety to form adducts by utilizing known process conditions. It is suitable to prepare the adduct by reaction in a solvent, if desired, at a temperature ranging from ambient to about 150° C. Representative examples of useful solvents include pyridine, dimethylformamide, tetrahydrofuran, triethylamine, ethers, methylene chloride and the like, with pyridine being preferred. Also, if desired, any of the several types of catalysts known to be useful in forming urethanes, ureas, thioureas and amides can be employed. Useful catalysts include tertiary amines, salts or organic acids with a variety of metals such as alkali metals and the like.

The oxazine urea chromophors of the invention were coupled to biological or clinical compounds of interest through the Z moiety in various ways to form adducts. For example, when the Z moiety is isocyanate, as in isocyanatohexyl-Nile blue O urea, the chormophor is well-suited to coupling with an organic substrate containing a functional group having an active hydrogen group selected from the group consisting of hydroxyl, amino, sulfydryl and carboxylic. Typical organic substrates are digoxin, cortisol, estradiol and, in general, drugs or hormones having reactive hydroxyl groups. For example, cortisol can be coupled to isocyanatohexyl-ureado-Nile blue O in accordance with the invention by a carbamate bond as shown in the following equation:

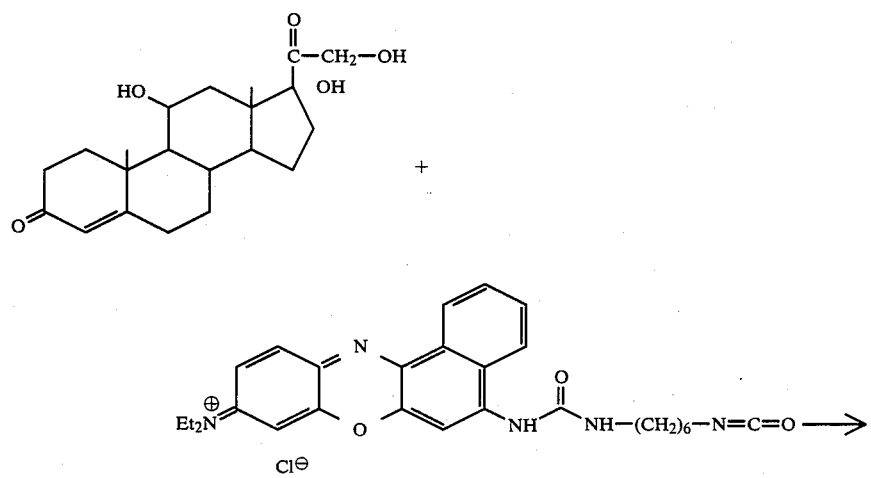

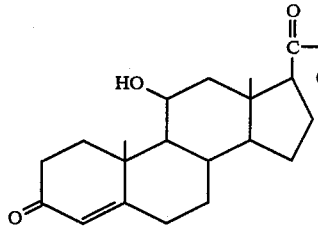
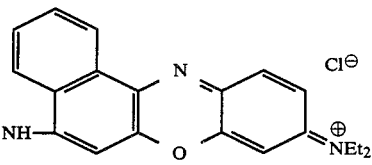

Thus, in accordance with the present invention adducts of urea derivatives of oxazine and thiazine chromophors and organic substrates can be illustrated by the following general formula II:

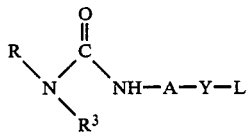

II wherein R represents the oxazine or thiazine chromophor; $R^3$ is hydrogen or alkyl of from 1 to 10 carbon atoms; Y is oxygen, sulfur or a primary or secondary amine group of from 1 to 12 carbon atoms; L is an organic substrate; and A is a divalent group selected from the class consisting of:

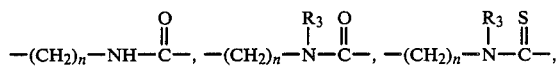

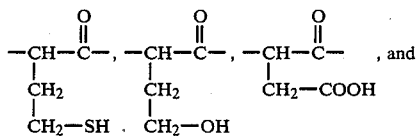

-continued

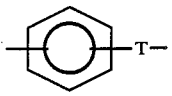

wherein T represents

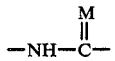

$-NR^3$ and $$-NH-\overset{M}{\underset{\|}{C}}-$$

wherein M and n are as previously indicated.

Illustrative of the novel adducts encompassed by formula II include:

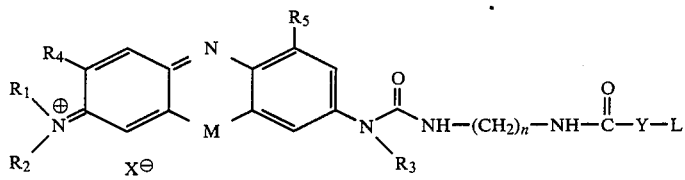

wherein n, M, $R_1$, $R_2$, $R_3$, $R_4$, $R_5$ and $X^\ominus$ are the same as hereinbefore defined, Y is O, primary or secondry amine group, or S; L is an organic substrate containing a functional group having an active hydrogen selected from the group consisting of hydroxyl, amino, sulfhydryl, and carboxylic.

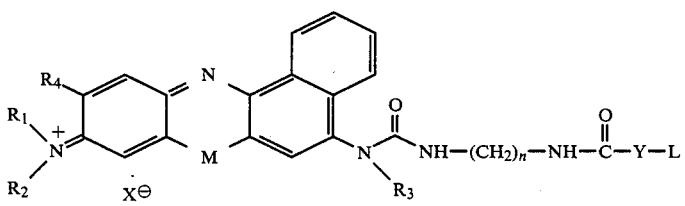

wherein n, M, $R_1$, $R_2$, $R_3$, $R_4$ and $X^\ominus$ Y and L are the same as defined,

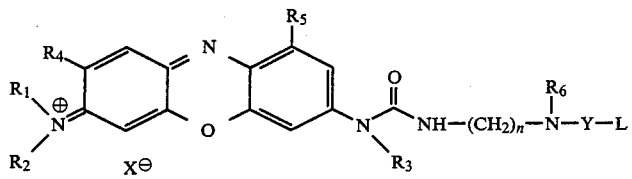

wherein n, M, $R_1$, $R_2$, $R_3$, $R_4$, $R_5$, and $X^\ominus$ are the same as hereinbefore defined, $R_6$ is hydrogen, alkyl or aryl; Y is

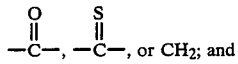, or $CH_2$; and when Y is

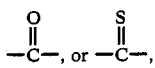,

L is an organic substrate containing an active carboxylic, thiocarboxylic or dithiocarboxylic group and when Y is $CH_2$, L is an organic substrate containing an active halogen group.

or aryl; and L is an organic substrate containing a functional group having an active hydrogen selected from the group consisting of primary or secondary amino groups.

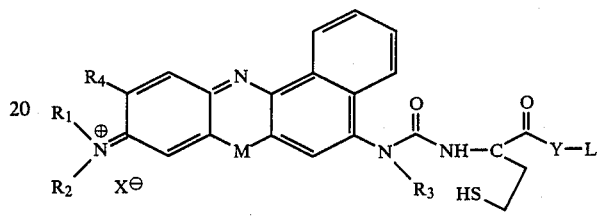

wherein M, $R_1$, $R_2$, $R_3$, $R_4$, $X^\ominus$, Y and L are as defined above.

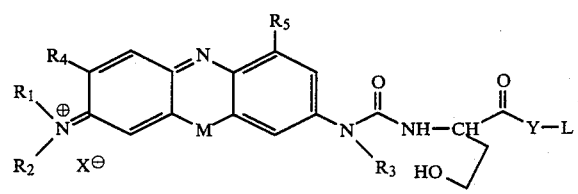

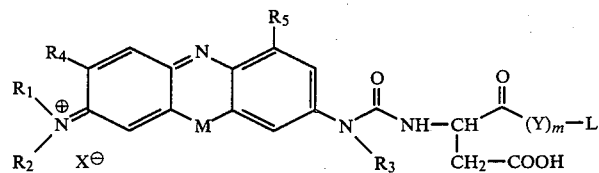

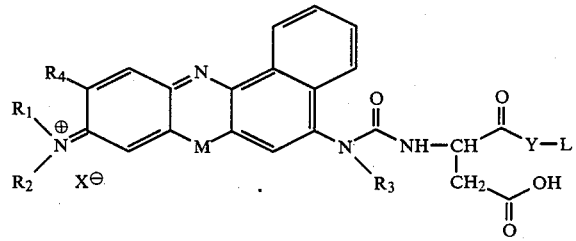

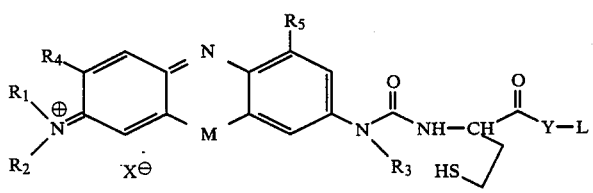

wherein n, M, $R_1$, $R_2$, $R_3$, $R_4$, $R_5$ and $X^\ominus$ are as hereinbefore defined; Y is NH or NR', wherein R' is an alkyl wherein M, $R_1$, $R_2$, $R_3$, $R_4$, $R_5$, $X^\ominus$, Y and L are as defined.

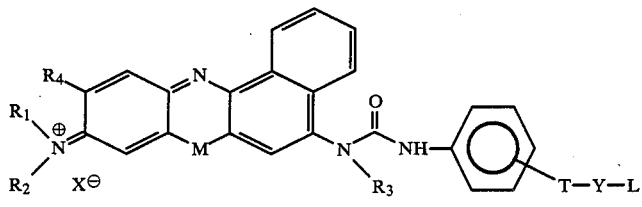

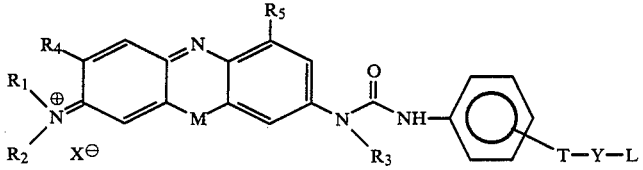

wherein M, $R_1$, $R_2$, $R_3$, $R_4$, $R_5$, and $X^\ominus$ are as defined claim 1; L is an organic substrate containing a functional group having an active hydrogen selected from the group consisting of hydroxyl, amino, sulfydryl, carboxylic and halogen, and when T is

Y is NH, S, or R′N, wherein R′ is alkyl or aryl, and L is an organic substrate containing a hydroxy, amino, or sulfydryl group with active hydrogen; when T is NO or —NR³, Y is

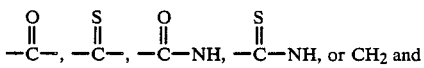

L is an organic substrate containing an active carboxylic, thiocarboxylic, isocyanato or isothiocynato and when Y is CH₂, L is an organic substrate containing an active halogen group. When T is —, Y is

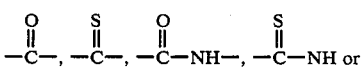

CH₂ and when Y is

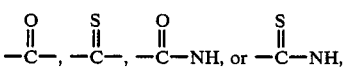

L is an organic substrate containing an active carboxylic, thiocarboxylic, or isocyanato group, and when Y is CH₂, L is an organic substrate containing an active halogen; when T is

Y is NH or R′N, and L is an organic substrate containing a functional group having an active hydrogen selected from the group consisting of hydroxyl or amino; and when T is

Y is NH or R′N, and L is an organic substrate containing a functional group having an active hydrogen selected from the group consisting of primary or secondary amino group.

The isocyanato-alkyl-ozaxine chromophors can be bound to organic substrates to form adducts by utilizing known process conditions. It is suitable, for exmple, to prepare the adduct by reaction in a solvent, if desired, at temperatures ranging from ambient to about 150° C. Representative examples of useful solvents which are inert to the isocyanato radicals include pyridine, tetrahydrofuran, dimethylformamide, triethylamine, ethers, methyleneechloride and the like with pyridine being preferred. Also, if desired, any of the several types of catalysts known to be useful in forming urethanes, ureas, thioureas and amides can be employed. Useful catalysts include tertiary amines, salts or organic acids with a variety of metals such as alkali metals and the like. The conditions selected should be such as to insure that the structure of the compound or substrate of interest will not be degraded or otherwise adversely affected. For this reason, it is preferred to utilize as mild conditions as possible.

When the Z moiety is thiolactone as in butyrothiolactone-cresyl violet-urea, the resulting urea was well-suited to coupling with organic substrates having an active primary or secondary amine group. Typical organic substrates are proteins such as antibodies, enzymes, and drugs with active amine groups, receptive to an amide linkage. The following reaction of the thiolactone cresyl violet urea is illustrated:

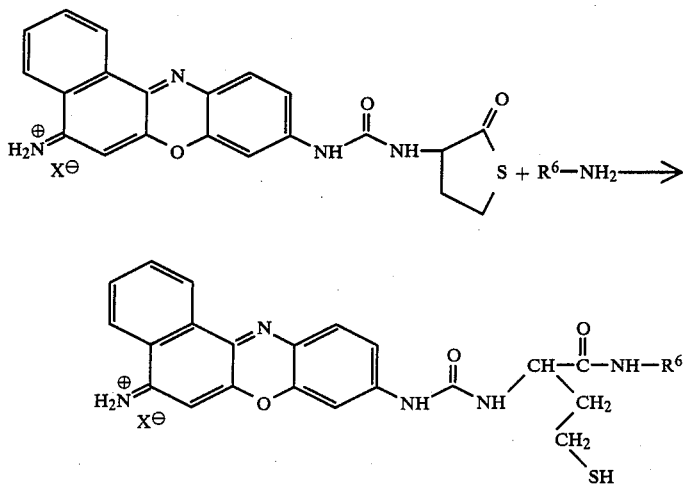

wherein $R^6$ is the residue of organic substrate L. This coupling was carried out in a variety of solvents depending on the nature of the amine substrate. The coupling of proteins was carried out in a variety of buffers, such as carbonates or phosphates. The pH of the reaction ranged from 1–12, but pH of 8 to 10 was preferred. The reaction time and temperature was appropriately selected depending on the stability and nature of the protein. The preferred reaction time was 1 to 24 hours and the preferred temperature was 4° C. to ambient. Since proteins may have more than one amino group, it is possible that more than one of the oxazine chromophors can be coupled. The coupling of one to five thiolactone-oxazine chromophors is preferred. The ratio of the chromophor to protein coupled can be controlled by the amount of the chromophor-thiolactone used. Other solvents such as, for example, pyridine formamides, amides, alcohols, ethers and chlorinated hydrocarbons inert to the reaction partners can be used where the nature of the organic substrate allows.

When the Z moiety is isothiocyanate, coupling occurs readily with an organic substrate containing a functional amine group having an active hydrogen which is receptive to thiourea linkage. The following reaction illustrates such a coupling.

The conditions for the thiourea coupling are similar to the conditions used for the coupling of thiolactone-oxazine-urea.

As previously set forth, a urea derivatization of the oxazine chromphor which lead to functionalization of the chromophors, serving in further couplings, does not effectively change their physical properties (e.g., excitation, emission). Adducts of oxazine-urea derivatives with organic substrates of interest are intended for use in many of the several known techniques involving fluorescent tagging or fluorescent competitive binding to detect and measure a compound or substrate of interest. The particular adducts used will be dependent upon the type of tagging required by the technique of choice, and the technique selected will be determined by the results as required. The ureado-oxazine adducts are particularly advantageous since they exhibit little deleterious effects on the biological compounds, emit at wavelengths which are above 600 nanometers and show little overlap between excitation and emission.

Thus, the compounds of the present invention can be conveniently coupled to an inert matrix or organic substrate by known techniques to provide novel conjugates or adducts as indicated above. The compounds can be coupled either directly or indirectly to the inert matrix or organic substrate, preferably a biological material, and hence render such compounds useful in a variety of

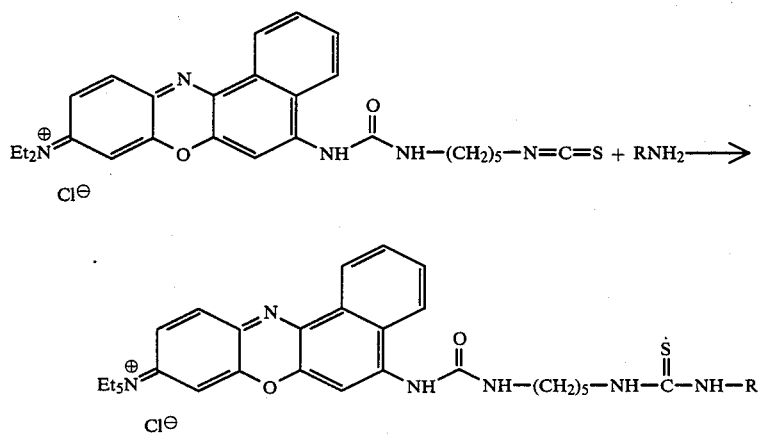

qualitative and quantitive determinations of one or more immunochemically reactive components in biological systems. Therefore, the chromophoric compounds can be coupled to a wide variety of biologically acceptable substrates which are normally employed in the detection and measurement of biological compounds. The only requirement of the matrix or substrate is that it contain one or more active sites through which coupling with the chromophoric derivative can be effected. In practice, such sites usually contain an active hydrogen and include, but are not limited to, primary amines, secondary amines, hydroxyls groups mercapto groups and the like. As indicated, coupling of the chromophoric derivatives to the matrix or substrate is effected by methods known to those skilled in the art to which this invention pertains.

It is therefore possible to form conjugates of the chromophoric derivatives with a wide variety of organic substrates, including, drugs, antigens, antibodies, haptens, peptides, proteins, amino acids, gamma globulin, avidin, bovine serum albumen, conalbumen, enzymes, and the like. A particularly preferred inert substrate which is widely used in the detection and measurement of biological compounds is the spherical beads or particles employed in chromatographic analytical techniques. For example, the derivatives of this invention can be conveniently coated on, or sensitized to, small beads or particles such as those composed of polystyrene or other inert biological compositions.

The chromophoric derivatives of the present invention are therefore useful in a wide variety of areas as a biochemical tool for the detection and measurement of biological compounds, particularly, immunochemically reactive components, siuch as those found in body fluids, cells and cell components. For example, the derivatives can be employed as conjugates with an inert matrix or organic substrate for use in antigen-antibody assays. Molecules, such as fluorescein or rhodamine are currently employed for fluorescence microscopy in indirect immunocytochemistry. Due to their improved stability, resistance to bleaching and the wide spread between excitation and emission, the derivatives of the present invention are ideally suited for replacement of the fluorescein currently employed in fluorescent antibody determinations.

The present invention is also directed to an immunoassay wherein an immunochemically active compound is coupled directly or indirectly to the novel chromophoric derivatives of the present invention, whreby during or after a set period of time for the immunochemical reaction to occur, and possibly after separation of the free and bound labelled components, the quantity of the chromophoric compound is determined in the test medium, or a separated fraction thereof, and wherein the determination provides a qualitative and/or quantitative indication of the immunochemical reactive component to be determined.

Accordingly, one aspect of the present invention relates to a particularly attractive procedure for the qualitative and/or quantitative determination of an immunochemically reactive component, including antibodies, antigens, haptens, and the like in test media including animal or human body fluids, such as blood serum, urine, and the like, and animal and human cells and components thereof.

The invention therefore also includes novel immunochemical reagents, composed of the aforementioned derivatives which may be in the form of dispersions, or polymeric nuclei coated with the chromophoric derivative, to which an immunochemically reactive component has been attached directly or indirectly. Also included within the scope of the invention are test kits containing the aforesaid immunochemical reagent.

In practice, the immunochemically reactive component labelled with the chromophoric derivatives of the present invention are employed in "test kits" as reagents in combination with other known reagents for the qualitative and/or quantitative determination of components suchs as haptens, antigens, antibodies and the like, using known assay methods. For example conventional immunochemical test procedures such as competitive immunoassay, sandwich techniques, and those test based on the agglutination principle can utilize the derivatives of the present invention.

For instance, in a conventional competitive immunoassay, a test sample containing an unknown quantity of antigen is brought into contact with a certain quantity of the corresponding antigen labelled with a chromophoric compound and an antibody attached to an insoluble carrier which is directed against this antigen, or a certain quantity of antigen attached to an insoluble carrier and an antibody labelled with the chromophor directed against this antigen. Upon completion of the reaction, the quantity of the chromophor is determined in the free or bound fraction which provides an indication of the antigen to be determined.

The derivatives of the present invention are accordingly useful for the determination of a wide variety of immunochemical components of body fluids and cells and includes, but not limited to human chorinic gonadotropin (HCG), hepatitis Surface B antigen (HBsAg), human placental lactogen (HPL), human anti-Rubella sera, human prolactin (PRL), testosterone, human T-cell leukemia virus (HTLV), adult T-cell leukemia associated antigen producing cells, and the like. The derivatives of the present invention are also useful in conjunction with SDS gel electrophoresis for the study of peptide fragments from the cleavage of proteins. In such studies, chromatography and electrophoresis provide a 2-dimensional map or "fingerprint" diagnosis of a protein.

The derivatives of the present invention are also useful as a replacement for radioactive tracers in automated electrophoresis processes such as those employed in determining the sequence of nucleid acids in genes. Newly available analytical instruments, such as the DNA sequencer developed at the California Institute of Technology are currently in use to expedite gene mapping of strands of DNA. In the current version of these instruments a laser and fluorescent dyes replace the use of radioactive materials and result in markedly increased savings in the time needed to effect the mapping. In the DNA sequencer amino acids exposed to intense light cause the dye to glow. By computer analysis of the intensity of color, the identity of the nucleic acid base can be determined. The chromophoric derivatives of the present invention are particularly attractive for this application due to their stability in the present of high intensity light such as the lasers employed in the DNA sequencer, and the distinct wide spread between the points of excitation and emission. Additionally, as previously indicated, the derivatives of the present invention are resistant to bleaching and hence are ideally suited for this application.

The following examples are illustrative but not in limitation of the present invention.

EXAMPLE 1

Isothiocyanato pentyl Nile blue A Urea

A mixture of 0.400 grams ($1.1 \times 10^{-3}$ mol) of Nile blue A and 0.3 milliliters (excess) of 1-isocyanato-5-isothiocyanato pentane was dissolved in 5.0 milliliters of dry pyridine and allowed to stir at ambient temperature for about 48 hours. The pyridine was then removed in vacuo at ambient temperature and the crude reaction mixture was washed with ether to remove unreacted 1-isocyanato-5-isothiocyanato pentane. Obtained was 0.520 grams of dark blue Nile blue A-isothiocyanate. IR (nujol) analysis showed bands at 3340 (NH), 2200 and 2130 (N=C=S), 1720, 1615, 1570, 1480, 1460, 1350, 1250, 1170, and 1010 $cm^{-1}$.

EXAMPLE 2

Isocyanatohexyl-Nile blue A Urea

A mixture of 450 mg of Nile blue A and 0.70 milliliters of 1,6-diisocyanato hexane was dissolved in 10 milliliters of dry pyridine and allowed to stir at ambient temperature for 6 days. The pyridine was then removed in vacuo at ambient temperature and the crude reaction mixture was washed with dry ether to remove unreacted diisocyanato hexane. 0.550 grams of isocyanatohexyl-Nile blue A-urea were obtained.

Since the isocyanato moiety was susceptible to hydrolysis, the product was used in its crude from. IR (pyridine) analysis showed bands of 3340 (NH), 2270 (N=C=O), 1700 $cm^{-1}$ (urea C=O).

EXAMPLE 3

N-(2-Thiolactone)-cresyl violet Urea

A mixture of 0.321 grams ($1.0 \times 10^{-3}$ mol) of cresyl violet acetate and 0.2 milliliter of 2-isocyanato butyrolactone were dissolved in 3 milliliter of dry methylene chloride and allowed to stir at ambient temperature for about 72 hours. The methylene chloride was then removed in vacuo and the product unreacted isocyanate. 0.400 grams was obtained of blue solid product. This product characterized by infrared spectroscopy showed bands of 1720 and 1690 $cm^{-1}$ (thiolactone), 1640 $cm^{-1}$ (urea).

EXAMPLE 4

Isothiocyanato pentyl-toluidine blue O-urea

A mixture of 0.600 grams of toluidine blue and 0.3 milliliters (excess) of 1-isocyanato-5-isothiocyanato pentane was dissolved in 10 milliliter of dry pyridine and allowed to stir at ambient temperature for 60 days. The solvent was then removed in vacuo and the crude reaction mixture was washed with ether to remove unreacted isocyanate. 0.5 grams of drak blue product was obtained. IR (nujol) analysis showed bands at 3300 (NH), 2200-2130 (N=C=S), 1660 (urea), and 1610 $cm^{-1}$ (aromatic).

EXAMPLE 5

Isothiocyanato pentyl-brilliant cresyl blue-urea

A mixture of 0.332 grams ($1 \times 10^{-3}$ mol) of brilliant cresyl blue. and 0.3 milliliter of 1-isocyanato-5-isothiocyanato pentane was dissolved in 5 milliliter of dry pyridine and allowed to stir at ambient temperature for 3 days. The solvent was removed in vacuo and the residue was washed with ether to remove unreacted 1-isocyanato-5-isothiocyanato pentane. 0.350 grams of product was obtained. IR (smear) analysis showed bands at 3.0μ (NH), 5.55–5.75 (N=C=S), 5.90, 6.08, 6.23 and 6.33μ.

EXAMPLE 6

Coupling of Nile blue-N-lactono-urea to protein

To 1.55 milliliters aliquot of a solution containing 10 milligrams of albumin in 0.5M sodiumcarbonate-sodiumbicarbonate buffer pH 9.5 was added dropwise 0.25 milliliters of a DMSO solution containing 10 milligrams of Nile blue-lactone and the mixture was stirred at ambient temperature over night. The mixture was then filtered through glasswool and a membrane filter (Gelman Acrodisc, 1.2 μm). Purification on a 2.5×18 cm sephadex G50 column using deionized water as eluent gave conjugate fraction which was liophylized and stored at 4° C.

EXAMPLE 7

Coupling of Cresyl Violet-N-2-lactono-urea to Protein

To 1.55 milliliters aliquot of a solution containing 10 milligrams of albumin in a 0.5M sodiumbiocarbonate-sodiumcarbonate buffer pH 9.5, was added dropwise 0.25 milliliters of a dimethylsulfoxide solution containing 10 milligrams of Cresylviolet-lactone, and the mixture was stirred at ambient temperature over night. The mixture was then filtered through glasswool and a membrane filter (Gelman acrodisc, 1.2 μm). Further purification on a 2.5×18 cm sephadex G50 column using deionized water as eluent gave conjugate fraction which was liophylized and stored at 4° C.

Although the invention has been illustrated by the preceding examples, it is not to be construded as being limited to the material employed therein, but rather, the invention is directed to the generic area as hereinbefore disclosed. Various modifications can be made without departing from the spirit or scope thereof.

What is claimed is:

1. An adduct of urea derivatives of oxazine and thiazine chromophors and an antibody, said adduct being selected from the group consisting of:

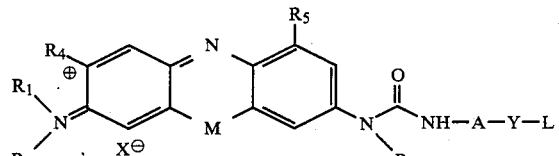

and

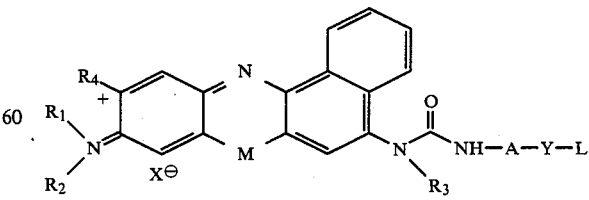

wherein $R^1$-$R^3$ are hydrogen or alkyl of 1 to 10 carbon atoms; $R^4$ and $R^5$ are $R^1$, halogen or amino; M is oxygen or sulfur; $X^-$ is an organic or inorganic anion; A is selected from the group consisting of:

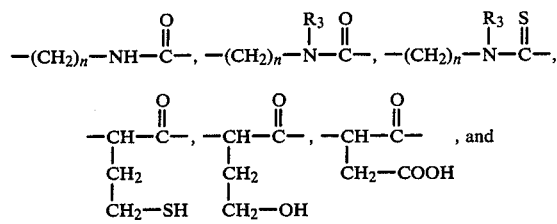

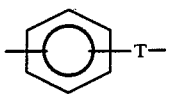, and

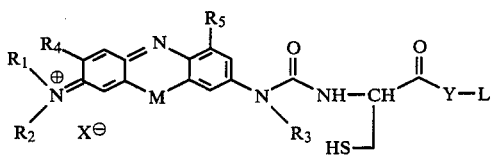

wherein T represents

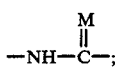

$NR^3$ and

—NH—$\overset{\overset{M}{\|}}{C}$—;

M represents oxygen or sulfur; Y is sulfur or a primary or secondary amine of from 1 to 12 carbon atoms; and L is an antibody.

2. An adduct as claimed in claim 1 having the formula:

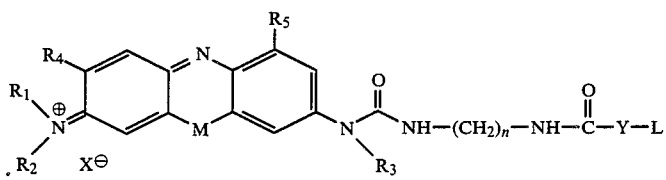

wherein $R^1$-$R^3$ are hydrogen or alkyl of 1 to 10 carbon atoms; $R^4$ and $R^5$ are $R^1$, halogen or amino; M is oxygen or sulfur; $X^-$ is an organic or inorganic anion; Y is sulfur or a primary or secondary amino of from 1 to 12 carbon atoms; L is an antibody having at least one active group capable of bonding to said oxazine and thiazine urea derivatives through Y, said active group being selected from the group consisting of hydroxyl, carboxyl, thiocarboxyl, dithiocarboxyl, halogen amino, isocyanato, isothiocyanato, mercapto and sulfahydryl; and n is 0 to 20.

3. An adduct as claimed in claim 1 having the formula:

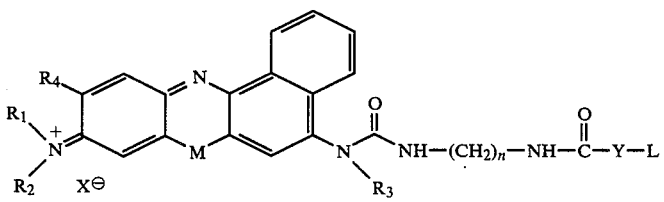

wherein $R^1$-$R^3$ are hydrogen or alkyl of 1 to 10 carbon atoms; $R^4$ and $R^5$ are $R^1$, halogen or amino; M is oxygen or sulfur; $X^-$ is an organic or inorganic anion; Y is sulfur or a primary or secondary amine of from 1 to 12 carbon atoms; L is an antibody having at least one active group capable of bonding to said oxazine and thiazine urea derivatives through Y, said active group being selected from the group consisting of hydroxyl, carboxyl, thiocarboxyl, dithiocarboxyl, halogen amino, isocyanato, isothiocyanato, mercapto and sulfahydryl; and n is 0 to 20.

4. An adduct as claimed in claim 1 having the formula:

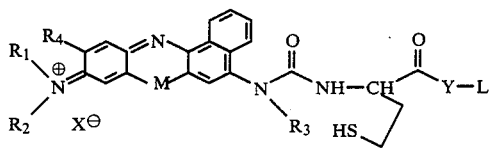

wherein $R^1$-$R^3$ are hydrogen or alkyl of 1 to 10 carbon atoms; $R^4$ and $R^5$ are $R^1$, halogen or amino; M is oxygen or sulfur; $X^-$ is an organic or inorganic anion; Y is sulfur or a primary or secondary amine of from 1 to 12 carbon atoms; L is an antibody having at least one active group capable of bonding to said oxazine and thiazine urea derivatives through Y, said active group being selected from the group consisting of hydroxyl, carboxyl, thiocarboxyl, dithiocarboxyl, halogen amino, isocyanato, isothiocyanato, mercapto and sulfahydryl.

5. An adduct as claimed in claim 1 having the formula:

wherein $R^1$-$R^3$ are hydrogen or alkyl of 1 to 10 carbon atoms; $R^4$ and $R^5$ are $R^1$, halogen or amino; M is oxygen or sulfur; $X^-$ is an organic or inorganic anion; Y is sulfur or a primary or secondary amine of from 1 to 12 carbon atoms; L is an antibody having at least one active group capable of bonding to said oxazine and thiazine urea derivatives through Y, said active group being selected from the group consisting of hydroxyl, carboxyl, thiocarboxyl, dithiocarboxyl, halogen amino, isocyanato, isothiocyanato, mercapto and sulfahydryl.

6. An adduct as claimed in claim 1 having the formula:

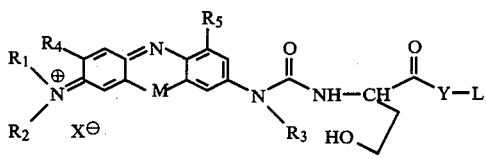

wherein $R^1$-$R^3$ are hydrogen or alkyl of 1 to 10 carbon atoms; $R^4$ and $R^5$ are $R^1$, halogen or amino; M is oxygen or sulfur; $X^-$ is an organic or inorganic anion; Y is sulfur or a primary or secondary amine of from 1 to 12 carbon atoms; L is an antibody having at least one active group capable of bonding to said oxazine and thiazine urea derivatives through Y, said active group being selected from the group consisting of hydroxyl, carboxyl, thiocarboxyl, dithiocarboxyl, halogen amino, isocyanato, isothiocyanato, mercapto and sulfahydryl.

7. An adduct as claimed in claim 1 having the formula:

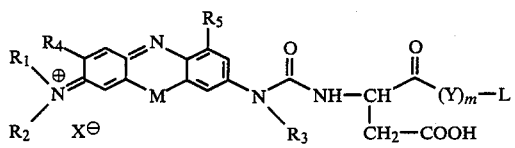

wherein $R^1$-$R^3$ are hydrogen or alkyl of 1 to 10 carbon atoms; $R^4$ and $R^5$ are $R^1$, halogen or amino; M is oxygen or sulfur; $X^-$ is an organic or inorganic anion; Y is sulfur or a primary or secondary amine of from 1 to 12 carbon atoms; L is an antibody having at least one active group capable of bonding to said oxazine and thiazine urea derivatives through Y, said active group being selected from the group consisting of hydroxyl, carboxyl, thiocarboxyl, dithiocarboxyl, halogen amino, isocyanato, isothiocyanato, mercapto and sulfahydryl; and m is 0 or 1.

8. An adduct as claimed in claim 1 having the formula:

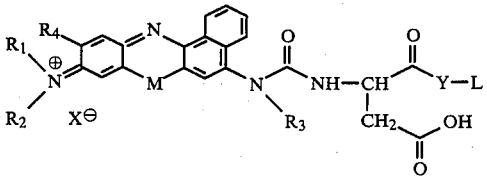

wherein $R^1$-$R^3$ are hydrogen or alkyl of 1 to 10 carbon atoms; $R^4$ and $R^5$ are $R^1$, halogen or amino; M is oxygen or sulfur; $X^-$ is an organic or inorganic anion; Y is sulfur or a primary or secondary amine of from 1 to 12 carbon atoms; L is an antibody having at least one active group capable of bonding to said oxazine and thiazine urea derivatives through Y, said active group being selected from the group consisting of hydroxyl, carboxyl, thiocarboxyl, dithiocarboxyl, halogen amino, isocyanato, isothiocyanato, mercapto and sulfahydryl.

* * * * *